United States Patent
Bjorndal et al.

(10) Patent No.: US 7,964,391 B2
(45) Date of Patent: *Jun. 21, 2011

(54) AUTOMATED, FIELD-PORTABLE SYSTEM FOR CONDUCTING TOXICITY MEASUREMENTS IN WATER, SOILS, AND SEDIMENTS

(75) Inventors: Bryan Bjorndal, Carlsbad, CA (US); David Lapota, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 1218 days.

This patent is subject to a terminal disclaimer.

(21) Appl. No.: 11/641,343

(22) Filed: Dec. 19, 2006

(65) Prior Publication Data

US 2008/0085506 A1     Apr. 10, 2008

Related U.S. Application Data

(63) Continuation-in-part of application No. 11/603,656, filed on Nov. 22, 2006, now Pat. No. 7,838,212, which is a continuation-in-part of application No. 11/586,747, filed on Oct. 10, 2006, now abandoned, and a continuation-in-part of application No. 11/586,745, filed on Oct. 10, 2006, now Pat. No. 7,704,731.

(51) Int. Cl.
    *C12M 1/34* (2006.01)
(52) U.S. Cl. .................... 435/288.7; 435/286.7
(58) Field of Classification Search ............. 435/286.7, 435/288.7
    See application file for complete search history.

(56) References Cited

U.S. PATENT DOCUMENTS

| | | | | |
|---|---|---|---|---|
| 4,774,055 A * | 9/1988 | Wakatake et al. | ............. | 422/64 |
| 4,950,594 A | 8/1990 | Stiffey | | |
| 5,565,360 A * | 10/1996 | Lapota et al. | ............. | 435/286.7 |
| 6,133,021 A * | 10/2000 | Gu et al. | ............. | 435/288.7 |
| 7,704,731 B2 * | 4/2010 | Bjorndal et al. | ............. | 435/288.7 |
| 2003/0194349 A1 * | 10/2003 | Carey et al. | ............. | 422/63 |
| 2004/0185549 A1 * | 9/2004 | Fujita et al. | ............. | 435/287.2 |

OTHER PUBLICATIONS

Cussatlegras et al., "Bioluminescence of the dinoflagellate Pyrocystic noctiluca induced by laminar and turbulent Couette flow", 2004, Journal of Experimental Marine Biology and Ecology, 310, pp. 227-246.*

B. M. Sweeney, F. T. Haxo, and J. W. Hastings; Action Spectra for Two Effects of Light on Luminescence in Gonyaulax polyedra; The Journal of General Physiology; Nov. 1, 1959, vol. 43, pp. 285-299.

(Continued)

*Primary Examiner* — Michael A Marcheschi
*Assistant Examiner* — Jonathan M Hurst
(74) *Attorney, Agent, or Firm* — Kyle Eppele; J. Eric Anderson (57) ABSTRACT

A system for testing the toxicity of a test sample comprising: an aqueous suspension of dinoflagellates; a test chamber configured to contain the aqueous suspension of dinoflagellates and the test sample; an optical signal generator configured to emit an excitation signal for exciting the dinoflagellates to emit a fluorescence signal if the dinoflagellates are alive; a first optical transducer configured to produce a first data signal in response to detecting the fluorescence signal; a stimulator configured to introduce a gas into the aqueous suspension for stimulating the dinoflagellates to emit a bioluminescence signal if the dinoflagellates are alive; a second optical transducer configured to produce a second data signal in response to detecting the bioluminescence signal; and a processor configured to compare the first data signal and the second data signal to a control data to generate an output representing the toxicity of the test sample.

17 Claims, 12 Drawing Sheets

OTHER PUBLICATIONS

J. Woodland Hastings and Beatrice M. Sweeney; On the Mechanism of Temperature Independence in a Biological Clock; Proc. N. A. S.; Jul. 14, 1957, vol. 43, pp. 804-811.

Robert W. Sabate, Arthur V. Stiffey, and Edmund L. Devvally: Bioluminesence in Toxicity Testing; 46 Environmental Geoscrences, vol. 2, No. 1, pp. 46-53; 1995.

* cited by examiner

AUTOMATED, FIELD-PORTABLE SYSTEM FOR CONDUCTING TOXICITY MEASUREMENTS IN WATER, SOILS, AND SEDIMENTS

CROSS-REFERENCE TO RELATED APPLICATIONS

This application is a continuation in part of U.S. Pat. No. 7,838,212, filed Nov. 22, 2006, entitled "Apparatus and Method for Providing Live Dinoflagellates for Toxicity Tests," which is a continuation in part of both U.S. application Ser. No. 11/586,747, filed Oct. 10, 2006, entitled "Method for Stimulation of Bioluminescent Organisms Via Turbulence Created by Gas Bubbles" and U.S. application Ser. No. 11/586,745, now U.S. Pat. No. 7,704,731, filed Oct. 10, 2006, entitled "System and Method for Quantifying Toxicity in Water, Soil, and Sediments" (Parent Application 2) All of these applications are hereby incorporated by reference herein in their entirety for their teachings.

FEDERALLY-SPONSORED RESEARCH AND DEVELOPMENT

This invention was developed with federal funds and is assigned to the United States Government. Licensing and technical inquiries may be directed to the Office of Patent Counsel, Space and Naval Warfare Systems Center, San Diego, Code 20012, San Diego, Calif., 92152; telephone (619) 553-3001, facsimile (619) 553-3821.

BACKGROUND OF THE INVENTION

Current systems for determining the toxicity of soils, sediments, and water tend to be complex, time consuming, and require the skill of a technician in a laboratory. As a result, current toxicity tests can be expensive, and prone to user error. A need exists for an easier, less expensive, quicker, more accurate, field-portable system for determining toxicity levels in soils, sediments, and water.

BRIEF DESCRIPTION OF THE DRAWINGS

Throughout the several views, like elements are referenced using like references. Figures are not drawn to scale.

DETAILED DESCRIPTION OF EMBODIMENTS

Figure 1:
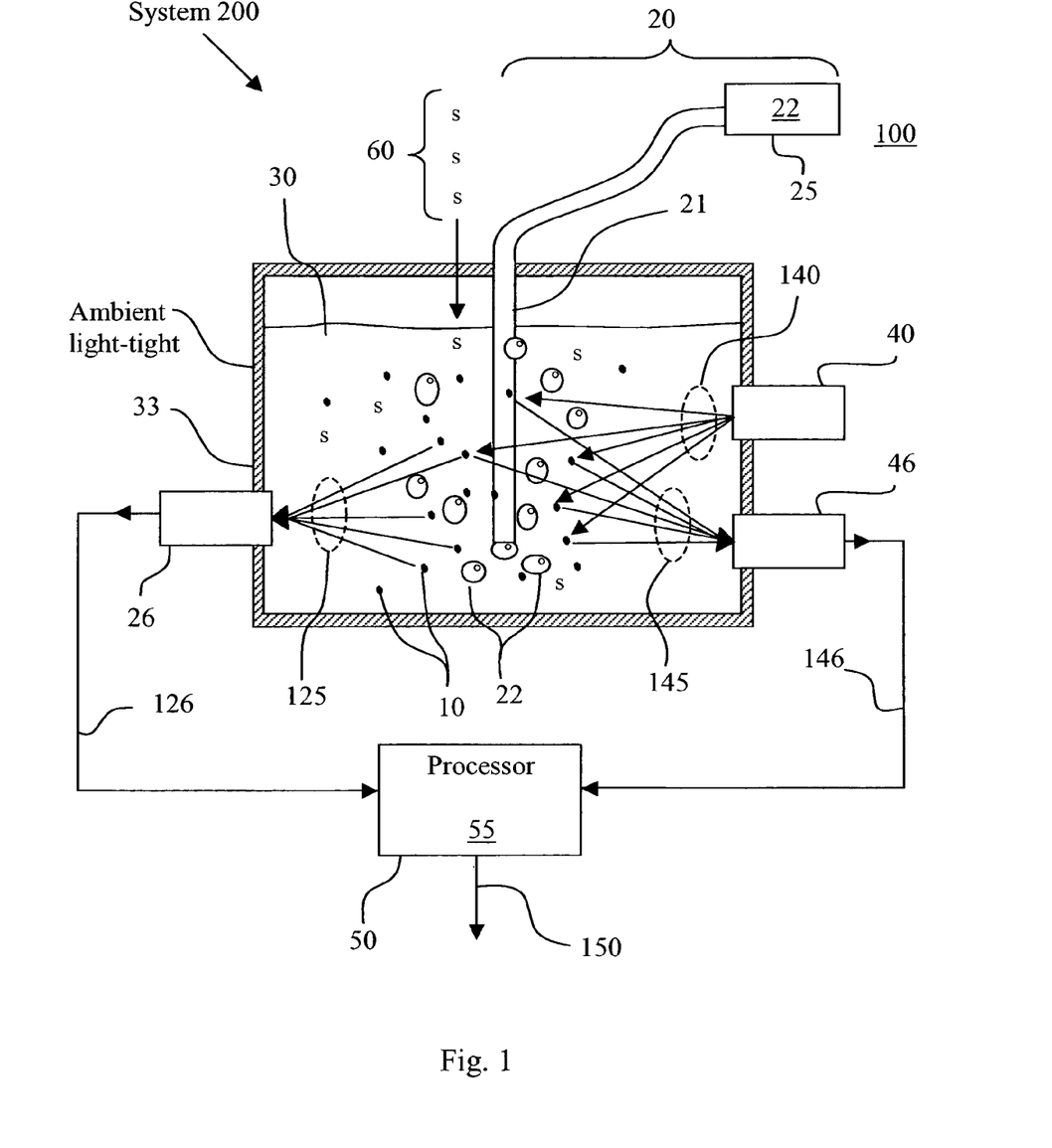
FIG. 1 shows an embodiment of a system for testing the toxicity of a test sample.

FIG. 1 shows a toxicity test system 200, a field-portable system for determining the toxicity of a test sample 60, such as water, soil and/or sediment. FIG. 1 shows how the test sample 60 may be added to an aqueous suspension 30 of dinoflagellates 10, which all may be contained in a test chamber 33. Inside the test chamber 33, if the dinoflagellates 10 are alive, the dinoflagellates 10 may be excited to fluoresce by an excitation signal 140 generated by an optical signal generator 40. The fluoresce signal 145 emitted by the excited dinoflagellates 10 may be detected by a first optical transducer 46 that is configured to produce a first data signal 146 in response to detecting the fluorescence signal 145. The first data signal 146 may be sent to a processor 50 where the first data signal 146 may be compared to control data 55. The dinoflagellates 10, inside the test chamber 33, may also be stimulated by a gas 22 to emit a bioluminescence signal 125 if the dinoflagellates 10 are alive. The gas 22 may be introduced into the aqueous suspension 30 of dinoflagellates 10 by a stimulator 20 in such a way as to create pressure pulses in the aqueous suspension 30 that cause the dinoflagellates 10 to bioluminesce. The bioluminescence signal 125 may be detected by a second optical transducer 26 that is configured to produce a second data signal 126 in response to detecting the bioluminescence signal 125. The second data signal 126 may be sent to the processor 50 where the second data signal 125 may be compared with the control data 55. The second data signal 126 may also be correlated with the first data signal 146, as discussed below. Based on the first and second data signals 146 and 126, the processor may generate an output 150 representing the toxicity of the test sample 60.

The dinoflagellates 10 in aqueous suspension 30 may be any species of dinoflagellates that fluoresce in response to a stimuli and bioluminesce in response to shear-stress inducing pressure pulses. Example embodiments of dinoflagellates 10 include, but are not limited to, *Gonyaulax polyedra*, *Pyrocystis lunula*, *Pyrocystis fusiformis*, and *Pyrodinium bahamense*. These species may be maintained, prior to testing, in an enriched seawater medium according to American Society for Testing and Materials Standard Guide for Conducting Static 96-h Toxicity Tests with Microalgae (ASTM 1990). Any number of dinoflagellate cells 10 may be added to aqueous suspension 30 provided their bioluminescence and fluorescence responses are measurable. By way of example, the population density of dinoflagellates 10 may be in the range of about 1 to about 500 dinoflagellate cells per milliliter of aqueous suspension 30. For example, about 3 milliliters of aqueous suspension 30 may comprise about 600 dinoflagellates 10. In another example, about 3 milliliters of aqueous suspension 30 may comprise about 300 dinoflagellates 10.

FIG. 1 also shows that the test chamber 33 may be light tight such that most ambient light may not enter the test chamber 33. The optical signal generator 40, the first optical transducer 46, the stimulator 20, and the second optical transducer 26 may be operatively coupled to the test chamber 33 in such a way as to allow them to perform their respective functions while preventing most ambient light from entering the test chamber 33.

The optical signal generator 40 is configured to generate an excitation signal 140 for exciting the dinoflagellates 10 to emit a fluorescence signal 145. Example embodiments of the optical signal generator 40 include, but are not limited to, a laser, a light emitting diode (LED), and any other optical signal generator capable of stimulating dinoflagellates 10 to emit fluorescence signal 145. The excitation signal 140 may be any signal capable of exciting the dinoflagellates 10 to emit a fluorescence signal 145. In one embodiment, the excitation signal 140 may be a continuous, blue, optical signal with a wavelength in the range of about 420 to about 440 nanometers configured to propagate into the test chamber 33 exciting dinoflagellates 10 to emit a fluorescence signal 145 with a wavelength of about 663 nanometers.

The first optical transducer 46 may be operatively coupled to the test chamber 33 and configured to detect the fluorescence signal 145 from excited dinoflagellates 10 in the test chamber 33. In response to detecting the fluorescence signal 145, the first optical transducer 46 may then generate the first data signal 146, an electrical signal, which is representative of a characteristic of interest of the fluorescence signal 145. Characteristics of interest of the fluorescence signal 145 include, but are not limited to, intensity, duration, wavelength, and photon count. Example embodiments of the first optical transducer 46 include, but are not limited to, a photomultiplier tube, a photodiode, a charge-coupled device (CCD), and any other device capable of generating a first data signal 146 in response to detecting the fluorescence signal 145.

The stimulator 20 may be operatively coupled to the test chamber 33 such that the stimulator 20 is configured to stimulate the dinoflagellates 10 in the test chamber 33 to emit bioluminescence signal 125. The stimulator 20 may be any device capable of introducing gas 22 into aqueous suspension 30 in such a way as to create turbulence in the aqueous suspension 30 such that the dinoflagellates 10 are stimulated to emit the bioluminescent signal 125. Pressure pulses caused by the turbulence of gas 22 moving through aqueous suspension 30 may cause the dinoflagellates 10 to bioluminesce. As shown in FIG. 1, the stimulator 20 may comprise a gas source 25 and a gas tube 21 for introducing the gas 22 into the aqueous suspension 30. The gas source 25 may be a gas reservoir, a gas pump, or any source capable of providing gas 22. The gas tube 21 may be a tube, a nozzle, a pipe, or any other device capable of transporting gas 22 from the gas source 25 and introducing gas 22 into aqueous suspension 30. Suitable gases for the gas 22 include, but are not limited to, air, nitrogen, oxygen, carbon dioxide, or any other gas that is capable of inducing bioluminescence through turbulence. For example, in one embodiment, the gas 22 may be air and the gas source 25 may be an air pump that pumps air 22 from the surrounding environment 100 into aqueous suspension 30.

Introducing gas 22 into aqueous suspension 30 creates turbulence, which induces fluid shear stress in aqueous suspension 30, which serves to stimulate the dinoflagellates 10 to emit bioluminescence signal 125. The wavelength of the bioluminescence signal 125 will generally lie within the range of about 450 to about 500 nanometers. Fluid shear stress may be defined as a change in direction or pressure of the fluid surrounding the dinoflagellates 10. In one embodiment, turbulence may be created when the ratio X/V ranges from about 0.667 to about 6.667, where X equals the flow rate of gas 22 into the aqueous suspension 30, and V equals the volume of aqueous suspension 30. For example, in one embodiment, the volume of aqueous suspension 30 may be 3 milliliters and the flow rate of gas 22 into aqueous suspension 30 may be 7 milliliters per second.

The second optical transducer 26 is operatively coupled to the test chamber 33 such that the second optical transducer 26 is capable of detecting the bioluminescence signal 125 from excited dinoflagellates 10 in the test chamber 33, as shown in FIG. 1. In response to detecting the bioluminescence signal 125, the second optical transducer 26 may then generate the second data signal 126, which is representative of a characteristic of interest of the bioluminescence signal 125. Characteristics of interest of the bioluminescence signal 125 include, but are not limited to, intensity, duration, wavelength, and photon count. The second optical transducer 26 may be any device capable of generating the second data signal 126 in response to the bioluminescence signal 125. Example embodiments of the second optical transducer 26 include, but are not limited to, a photomultiplier tube, a photodiode, a CCD, and any other device capable of generating a bioluminescence data signal 126 in response to detecting the second signal 125.

The processor 50 may be any device capable of receiving and transforming the second data signal 126 and the first data signal 146 into an output 150, which represents the toxicity of the test sample 60. Transforming the second data signal 126 and the first data signal 146 into an output 150 may be accomplished by measuring the first and second data signals 146 and 126 against control data 55 or a known fluorescence and bioluminescence standard. Mean relative fluorescence, standard deviation, and the coefficient of variation may be calculated by the processor 50 for the aqueous suspension 30 of dinoflagellates 10 in the test chamber 33. Relative fluorescence, calculated as a percentage of control values, can be plotted over time during the test. Example embodiments of the processor 50 include, but are not limited to, a computer, and any other device capable of correlating the second data signal 126 and the first data signal 146 and generating an output 150 that represents the toxicity of the test sample 60. The output 150 may be any audio, visual, or tactile output capable of communicating to a user the toxicity of the test sample 60. Although FIG. 1 shows the output 150 as exiting the processor 50, it is to be understood that the output 150 may also be used as an input to an internal function of the processor 50, or used as an input to another device or system.

The processor 50 may also control the sequence of testing. For example, after the aqueous suspension 30 has been placed in the test chamber 33, the processor 50 may turn on the optical signal generator 40 to emit the excitation signal 140 for y seconds (where y is an integer). During the emission of excitation signal 140 the processor 50 may record the first data signal 146 generated by the first optical transducer 46 in response to detecting fluorescence signal 145. After y seconds, the optical signal generator 40 may be turned off and the stimulator 20 may be activated by the processor 50 to stimulate the dinoflagellates 10 to emit a bioluminescence signal 125. Once the stimulator 20 has introduced gas 22 into the aqueous suspension 30, the processor 50 may record the second data signal 126 generated by the second optical transducer 26 in response to detecting the bioluminescence signal 125 emitted by stimulated dinoflagellates 10. The fluorescence data signal 146 and the bioluminescence data signal 126 may be compared to previous test results or to control data 55 stored in a look-up-table stored in the processor 50 in order to generate the output 150.

Figure 2:
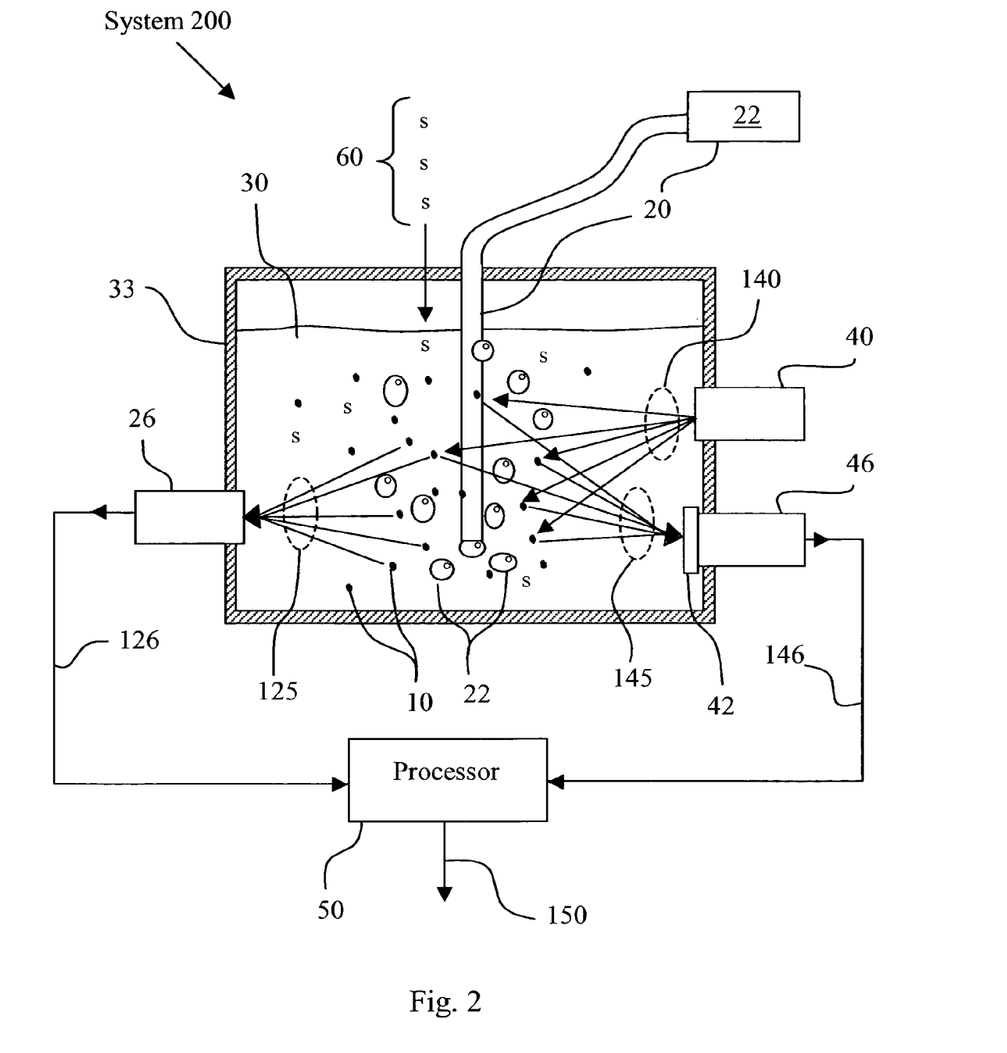
FIG. 2 shows a toxicity test system with a red optical filter.

FIG. 2 shows an embodiment of the toxicity test system 200 including a red optical filter 42 optically coupled between the dinoflagellates 10 and the first optical transducer 46. The red optical filter 42 may be any optical filter capable of preventing the excitation signal 140 from being detected by the first optical transducer 46 while allowing the fluorescence signal 145 to be transmitted through the red optical filter 42 to the first optical transducer 46. For example, the red optical filter 42 may be a wavelength-selective filter that only allows passage of optical signals falling within the range of about 660-690 nanometers.

Figure 3:
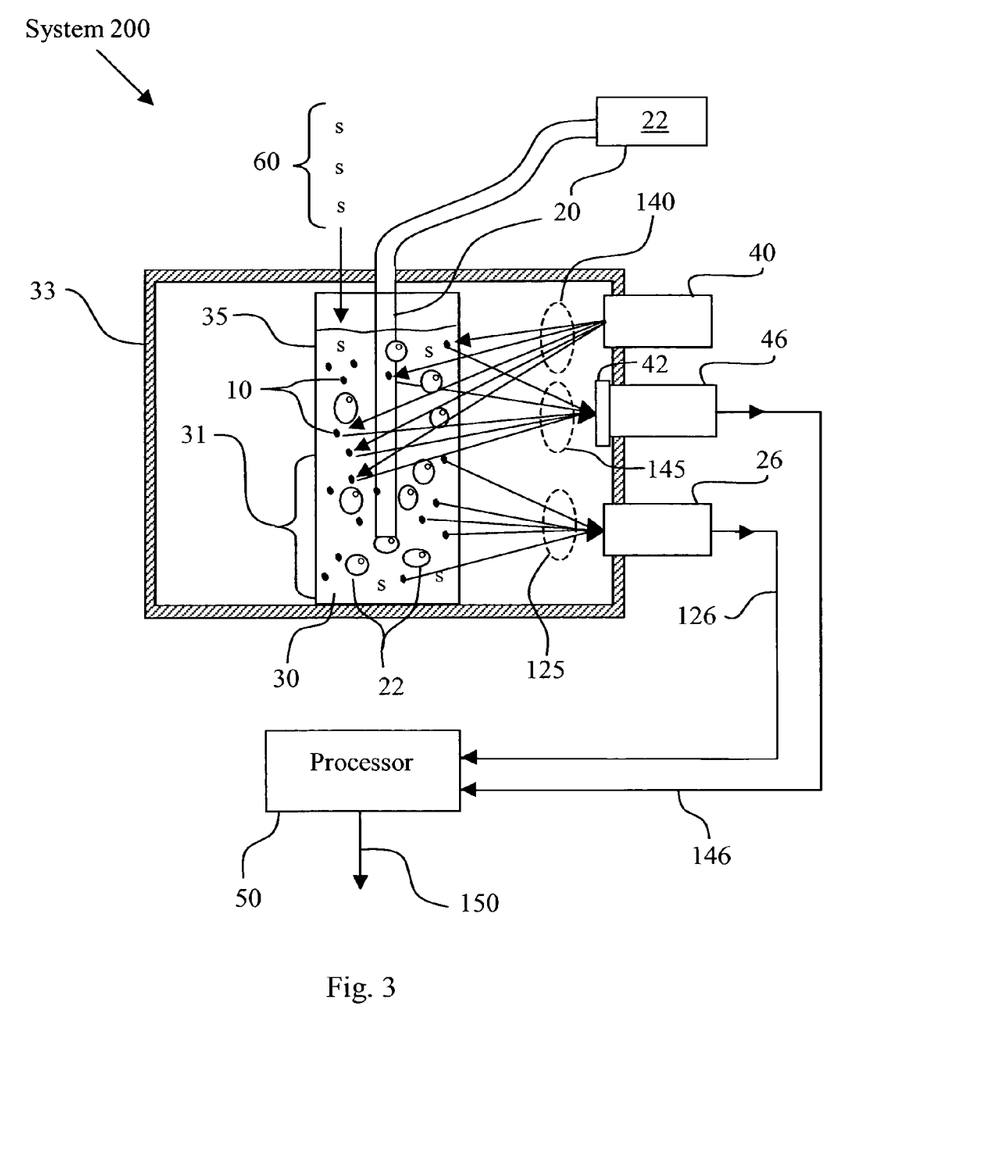
FIG. 3 shows a toxicity test system with a transparent sample container.

FIG. 3 illustrates another embodiment of system 200 where the aqueous suspension 30 and the test sample 60 may be contained in a removable, sample container 35. The sample container 35 is configured to be inserted into the test chamber 33. By way of example, the sample container 35 may be a test tube, a cuvette, or any other container capable of fitting inside the test chamber 33 and containing aqueous suspension 30.

The sample container 35 may be made of polystyrene, glass, polycarbonate, or any other material that is optically transparent to the wavelengths of the excitation signal 140, the fluorescence signal 145, and the bioluminescence signal 125. The sample container 35 may be made of a material which is chemically non-reactive with sea water, as for example, glass, DELRIN.RTM., polycarbonate, or polystyrene. The size and shape of the sample container 35 are limited only by the size and shape of the test chamber 33. The lower half of the sample container 35 may be defined as a lower end 31 into which the gas 22 may be introduced, as shown in FIG. 3.

Figure 4:
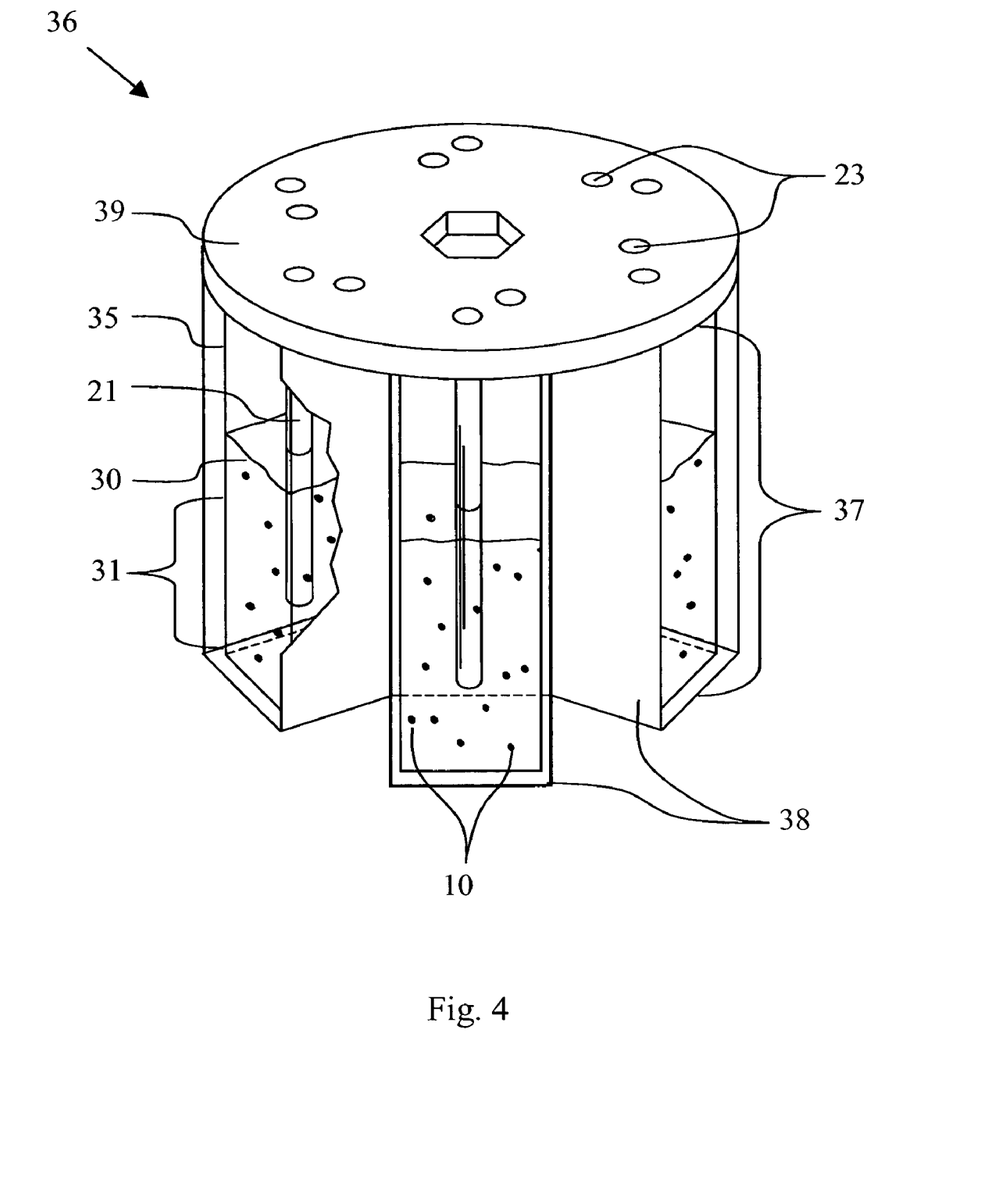
FIG. 4 shows a toxicity-test-system-compatible cartridge.

FIG. 4 shows a cartridge 36 that is configured to be supported inside the test chamber 33. The cartridge 36 comprises an array of sample containers 35. Each of the sample containers 35 contains a generally equal amount of the aqueous suspension 30 of dinoflagellates 10. As shown in FIG. 4, all of the sample containers 35 are optically isolated from each other by an array of optical isolation silos 38. Each optical isolation silo 38 comprises an optical window 37 through which the excitation signal 140, the fluorescence signal 145 and the bioluminescence signal 125 may pass. The cartridge 36 also comprises a cartridge cover 39 configured to cover each of the sample containers 35. In one embodiment, the cartridge cover 39 may comprise a vent 23 and a gas tube 21 for each of the sample containers. Each gas tube 21 extends into the lower end 31 of each sample container 35.

Figure 5:
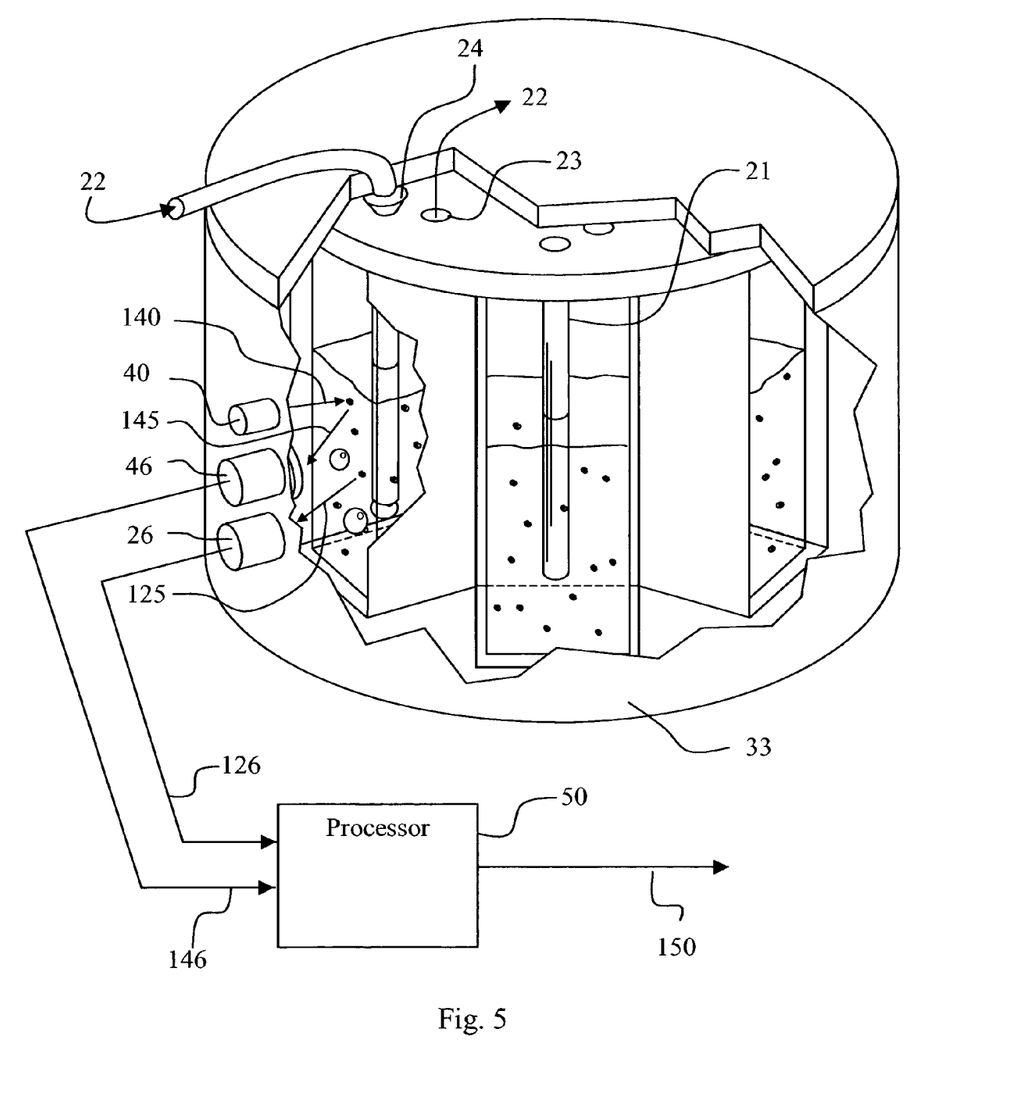
FIG. 5 is a perspective view of a cartridge in a test chamber.

FIG. 5 shows how the cartridge 36 may be operatively coupled to the toxicity test system 200 so that the gas 22 may be directed through the gas tube 21 into the aqueous suspension 30 in the lower end 31 of each of the sample containers 35. The gas vent 23 is configured to allow the gas 22 to escape from each of the sample containers 35. FIG. 5 also shows a first coupling nib 24 that is configured to direct the gas 22 from the gas source 25 to pass into the gas tube 21 of the sample container 35 with which the first coupling nib 24 is aligned. The first coupling nib 24 may be any device or structure that allows gas 22 from the gas source 25 to be directed into the gas tube 21 with which the first coupling nib is aligned.

Figure 6:
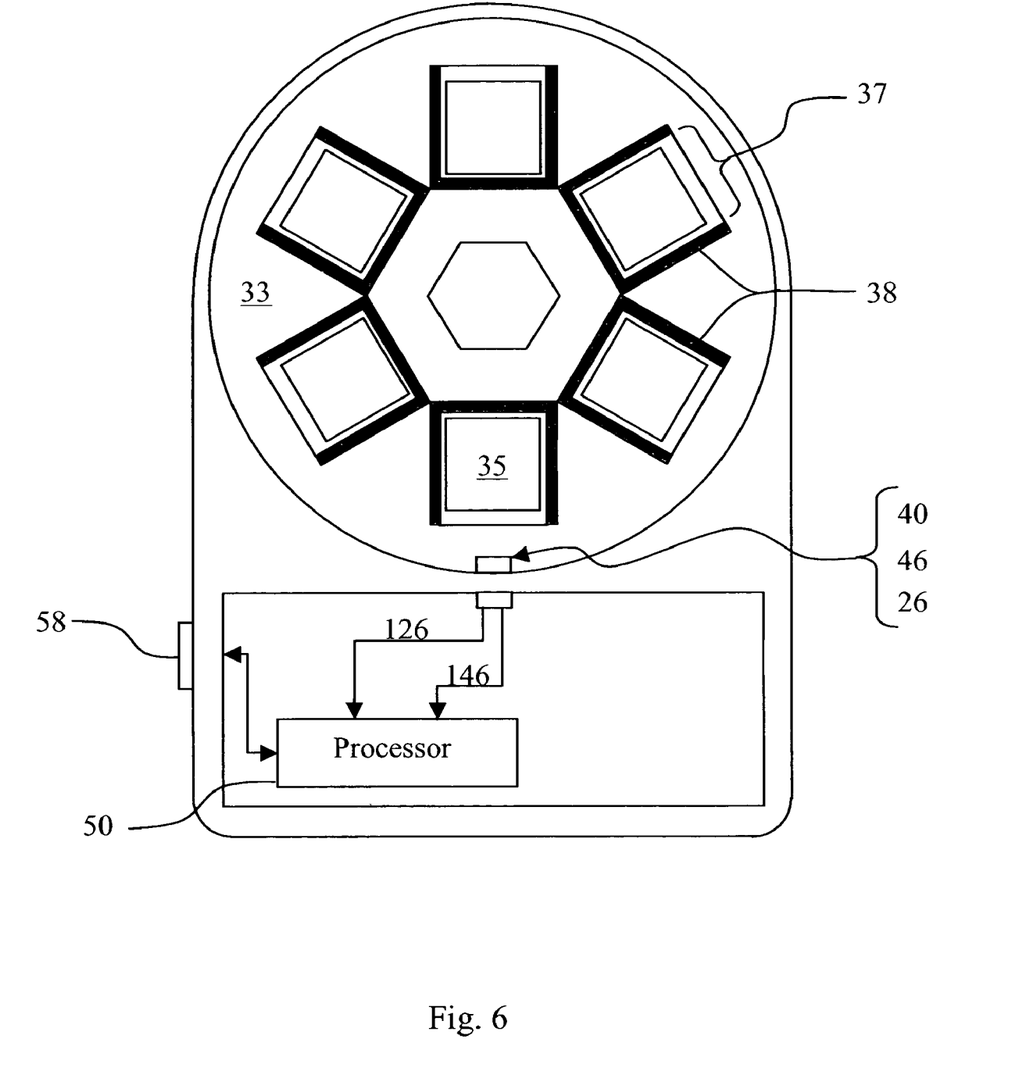
FIG. 6 is a top view of a cartridge in a test chamber.

FIG. 6 shows how each optical window 37 may be oriented on each optical isolation silo 38 such that only one optical window 37 at a time may be optically aligned with the optical signal generator 40, and the first and second optical transducers 46 and 26. Such an alignment provides that generally only the fluorescence and bioluminescence signals 145 and 125 emanating from one sample container 35 may be detected by the first and second optical transducers 146 and 126 respectively and that optical signals entering or exiting through the optical window 37 do not impinge on the sample containers 35 in other optical isolation silos 38. FIG. 6 also shows a communications interface 58 electrically coupled to the processor 50. The communications interface 58 may be a serial port, a USB port, or any other interface capable of 2-way communication with the processor 50. The output 150 may be communicated through the communications interface 58 to a remote processor.

Figure 7:
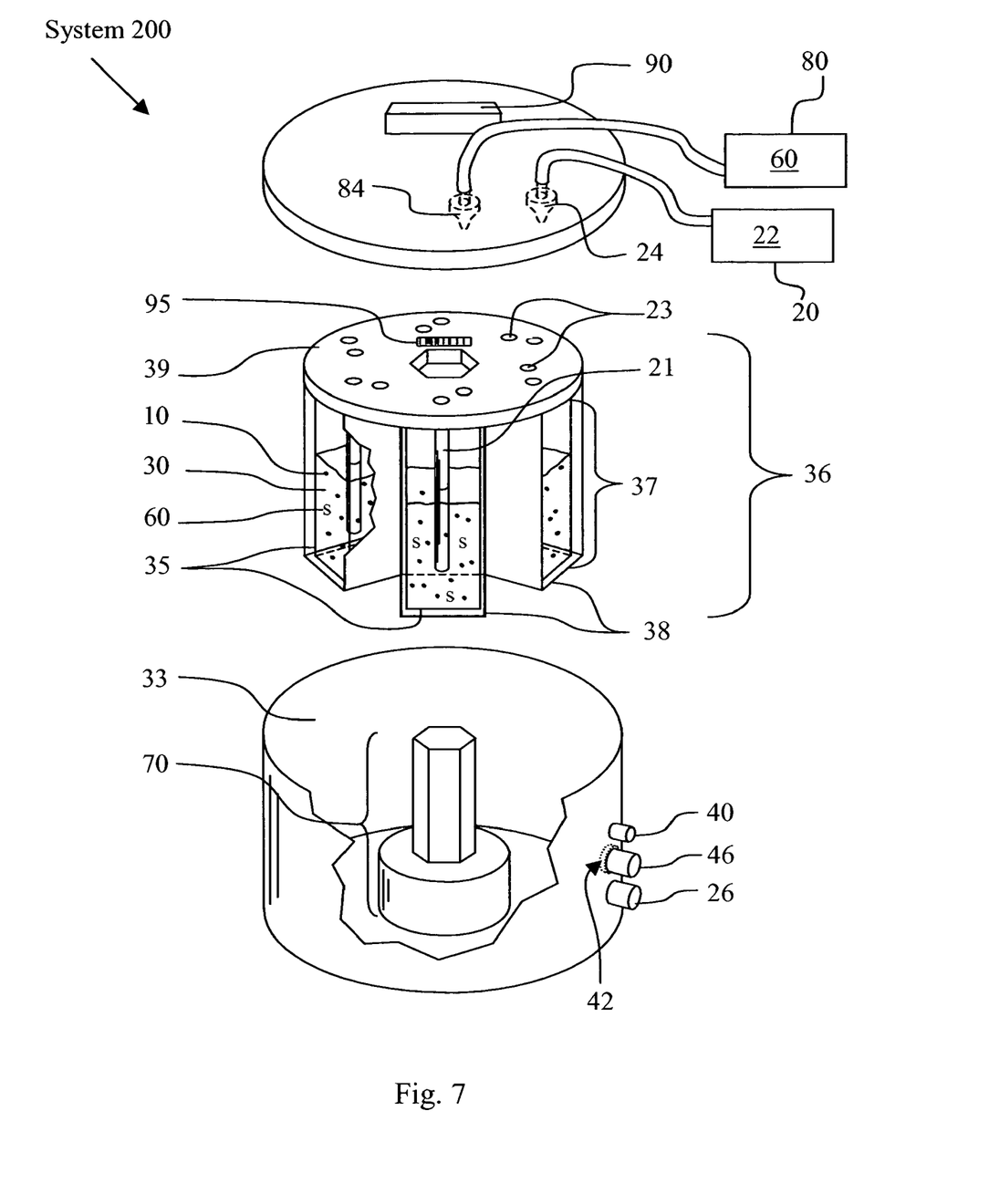
FIG. 7 is an expanded view of an embodiment of the toxicity test system.

FIG. 7 is an expanded view of one embodiment of the toxicity test system 200 further comprising an actuator 70 configured to reposition the cartridge 36 inside the test chamber 33 such that each of the optical windows 37 in turn may be optically aligned with the first and second optical transducers 46 and 26. The actuator 70 may be a servo, a stepper motor, or any other device capable of repositioning the cartridge 36 inside the test chamber 33 such that each of the optical windows 37 in turn may be optically aligned with the first and second optical transducers 46 and 26. As each of the optical windows 37 is optically aligned with the first and second optical transducers 46 and 26, their respective gas tubes 21 are aligned with the first coupling nib 24. Alignment of the gas tube 21 and the first coupling nib 24 allows gas 22 to be introduced into aqueous suspension 30 in the lower end 31 of the aligned sample container 35.

FIG. 7 also shows a bar code 95 affixed to an outer surface of the cartridge cover 39. The bar code 95 may contain cartridge 36 identification information. Also shown is a bar code scanner 90 configured to scan the bar code 95 and to convey cartridge 36 identification information to the processor 50. The bar code scanner 90 need not be mounted to the test chamber 33 as shown in FIG. 7, but may be configured in any way that allows the bar code scanner 90 to scan the bar code 95 whether inside or outside the test chamber 33.

FIG. 7 also shows a test sample distributor 80 configured to distribute an amount of the test sample 60 into each of the sample containers 35. The distributor 80 may be any dosing device capable of dispensing a predetermined amount of test sample 60 into each of the sample containers 35. In one embodiment, the test sample distributor 80 may be coupled to a second coupling nib 84, which may be aligned with the vent 23 of any one of the sample containers 35 to allow an amount of test sample 60 to be distributed to each of the sample containers 35. The processor 50 may control how much test sample 60 is distributed into each sample container 35.

Figure 8:
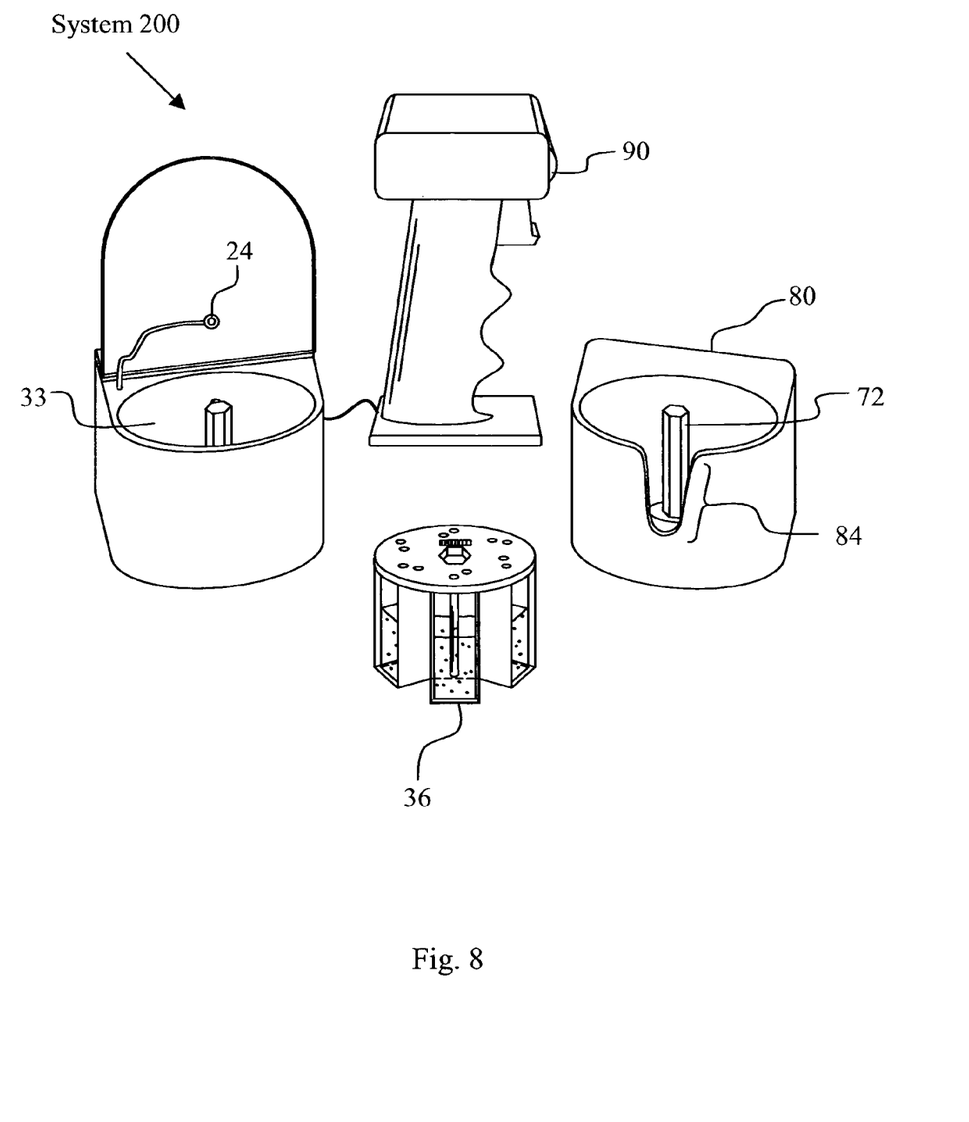
FIG. 8 shows a toxicity test system with a distributor and a bar code scanner.

FIG. 8 shows an alternative embodiment of the toxicity test system 200 wherein the distributor 80 and the bar code scanner 90 are separate from the test chamber 33. In this embodiment, the distributor 80 further comprises a second actuator 72 and a viewing window 84. When the cartridge 36 is placed in the distributor 80, a user may add an amount of the test sample 60 to the sample container 35 that is aligned with the viewing window 84. The second actuator 72 is configured to reposition the cartridge 36 in the distributor 80 such that each sample container 35 in the cartridge 36 may be aligned with the viewing window 84. In the embodiment shown in FIG. 8, the bar code scanner 90 may scan the bar code 95 on the cartridge 36 while the cartridge 36 is outside the test chamber 33.

Figure 9:
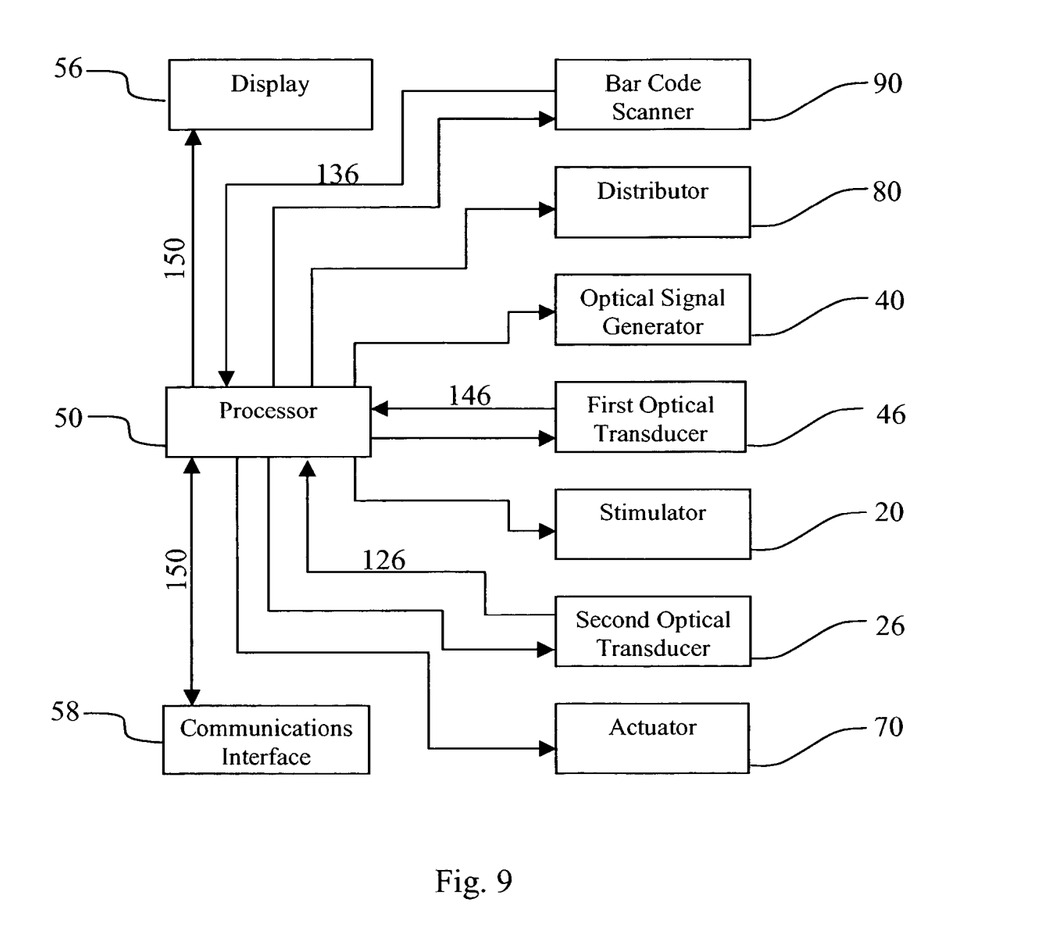
FIG. 9 is a block diagram showing the communication between a processor and other elements of a toxicity test system.

FIG. 9 is a block diagram outlining the communication of the various elements of the toxicity test system 200 with the processor 50. Also shown is an optional display 56, which is capable of displaying the output 150. The display 56 may be any audio, visual, or tactile display capable of conveying information to a user regarding the toxicity of the test sample 60. The display 56 may be operatively coupled to the test chamber 33 or be separate from it.

Figure 10:
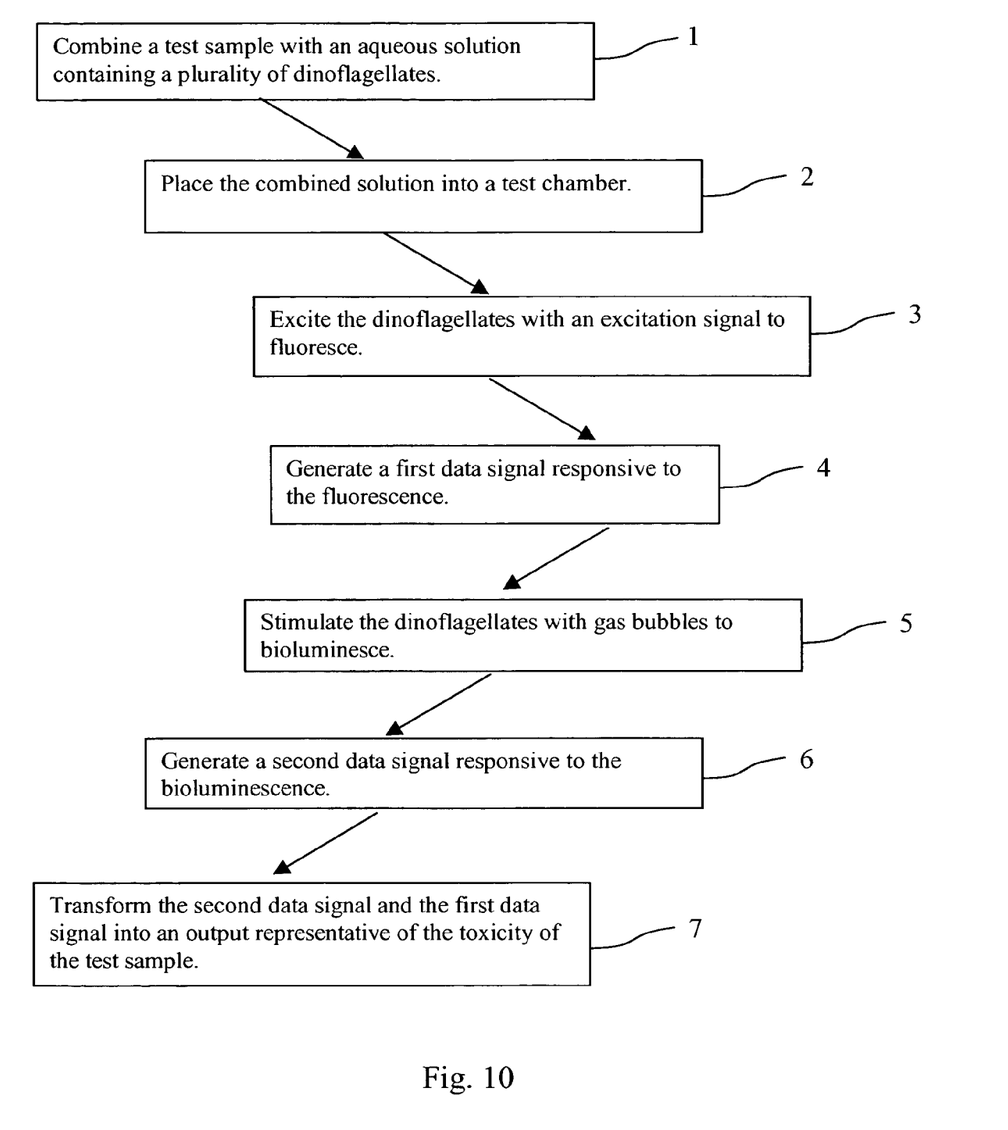
FIG. 10 is a flowchart of a method of using a toxicity test system to measure the toxicity of a test sample.

FIG. 10 illustrates how the toxicity test system 200 may be used to measure the toxicity of a test sample 60. In step one, the test sample 60 is combined with an aqueous suspension 30 containing a plurality of dinoflagellates 10. The combined suspension is then placed into the test chamber 33. Inside the test chamber 33, the dinoflagellates 10 are excited with an excitation signal 140 to fluoresce. In response to the fluorescence signal 145 emitted by the excited dinoflagellates 10, a first data signal 146 is generated. In step five, the dinoflagellates 10 are stimulated with gas 22 bubbles to bioluminesce. In response to the bioluminescence signal 125 emitted by the stimulated dinoflagellates 10, a second data signal 126 is generated. Then the first and second data signals 146 and 126 may be transformed into the output 150 representing the toxicity of the test sample 60.

Figure 11:
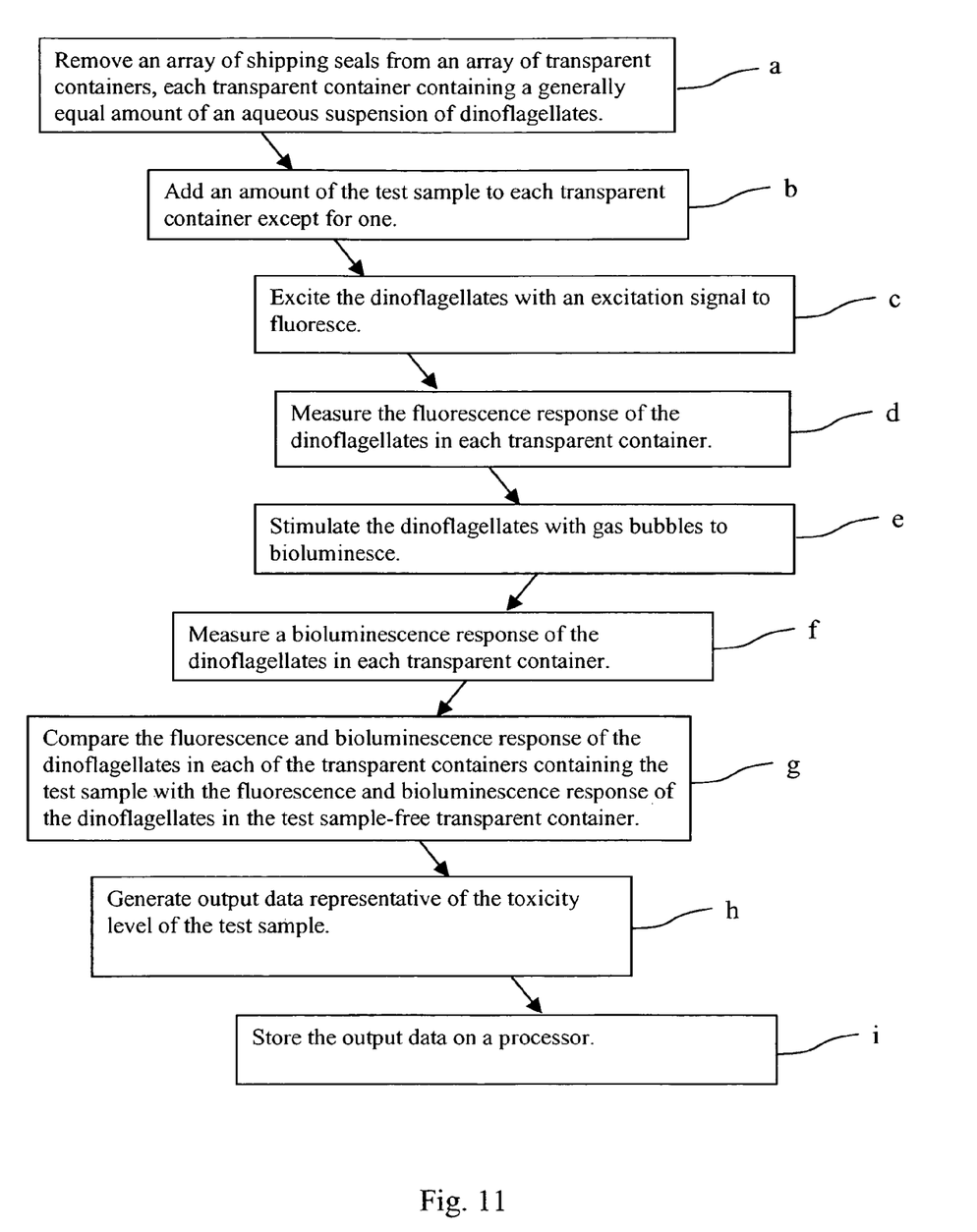
FIG. 11 is another flowchart of a method of using a toxicity test system to measure the toxicity of a test sample.
Figure 12:
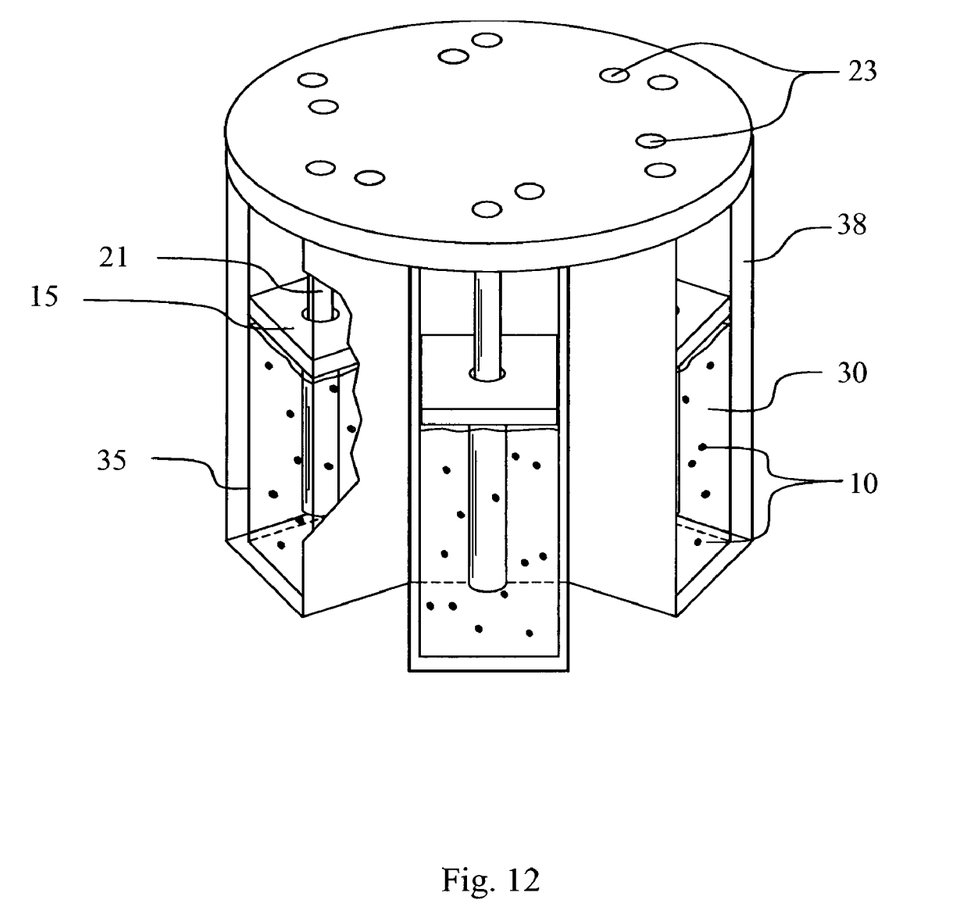
FIG. 12 shows a cartridge with shipping seals.

FIG. 11 illustrates how another embodiment of the toxicity testing system 200 may be used to measure the toxicity of a test sample 60. In step a, an array of shipping seals 15, as shown in FIG. 12 and described below, are removed from an array of sample containers 35. In step b, an amount of the test sample 60 may be added to each sample container 35 except for one. In step c, the dinoflagellates 10 are excited to fluoresce with an excitation signal 140. The fluorescence signal 145 emitted by the dinoflagellates 10 in each sample container 35 in response to the excitation signal 140 is then measured. In step e, the dinoflagellates 10 are stimulated to bioluminesce with gas 22 bubbles. The bioluminescence signal 125 emitted by the dinoflagellates 10 in each sample container 35 in response to the stimulation is then measured. In step g, the fluorescence and bioluminescence responses of the dinoflagellates 10 in each of the sample containers 35 containing the test sample 60 are compared with the fluorescence and bioluminescence responses of the dinoflagellates 10 in the test sample-free sample container 35. An output 150, representing the toxicity of the test sample 60 may then be generated and the output data may also be stored on the processor 50.

FIG. 12 shows the cartridge 36 with shipping seals 15 in place. The shipping seals 15 may be made of any material that is capable of preventing the aqueous suspension 30 from escaping the sample container 35. The shipping seal 15 may be mostly non-reactive with aqueous suspension 30 and the sample container 35. For example, the shipping seal 15 may be made of medical grade silicon. The shipping seal 15 may be any size or shape that is capable of sealing the sample container 35. FIG. 12 shows one embodiment where the shipping seal 15 is an elastomeric plug that may be inserted into each sample container 35 forming a seal. For this embodiment, the size and shape of the shipping seal 15 are such that its insertion into each sample container 35 creates a seal against the inner walls of each sample container 35—preventing the escape of aqueous suspension 30. The shipping seal 15 may enclose the gas tube 21, separating the aqueous suspension 30 from the gas tube 21.

After the bioluminescence and fluorescence responses have been measured for the dinoflagellates 10 in each sample container 35 in a cartridge 36, the cartridge 36 may be discarded and the process repeated with another cartridge 36. The bar code 95 on the cartridge 36 may be scanned with the bar code scanner 90 prior to testing. Also, after scanning and before the bioluminescence and fluorescence responses have been measured, the dinoflagellates 10 may be tested for viability by verifying a fluorescence response from the dinoflagellates 10. The verification of a fluorescence response may be accomplished by exciting the dinoflagellates 10 in the test chamber 33 with an excitation signal 140 and then measuring the fluorescence signal 145 produced by the dinoflagellates 10 in response to the excitation signal 140. After the dinoflagellates 10 have been tested for viability the process described above may begin. If the dinoflagellates 10 were tested and found to be not viable, the same scanning and viability testing procedure may be repeated with a new cartridge 36.

From the above description of the Automated Field-Portable System for Conducting Toxicity Measurements in Water, Soils, and Sediments, it is manifest that various techniques may be used for implementing the concepts of system 200 without departing from its scope. The described embodiments are to be considered in all respects as illustrative and not restrictive. It should also be understood that system 200 is not limited to the particular embodiments described herein, but is capable of many embodiments without departing from the scope of the claims.

We claim:

1. A system for testing the toxicity of a test sample comprising:
    an aqueous suspension of dinoflagellates;
    a test chamber configured to contain the aqueous suspension of dinoflagellates and the test sample;
    an optical signal generator configured to emit an excitation signal, the excitation signal disposed to excite the dinoflagellates to emit a fluorescence signal if the dinoflagellates are alive;
    a first optical transducer configured to produce a first data signal in response to detecting the fluorescence signal;
    a stimulator configured to introduce a gas into the aqueous suspension, wherein the stimulator comprises no moving parts, apart from the gas, that are in contact with the aqueous suspension, wherein the gas is disposed to stimulate the dinoflagellates to emit a bioluminescence signal if the dinoflagellates are alive;
    a second optical transducer configured to produce a second data signal in response to detecting the bioluminescence signal; and
    a processor configured to compare the first data signal and the second data signal to a control data to generate an output representing the toxicity of the test sample.

2. The system of claim 1, wherein ambient light is prevented from entering the test chamber.

3. The system of claim 2, further comprising a red optical filter optically coupled between the dinoflagellates and the first optical transducer.

4. The system of claim 3, wherein the gas is disposed to form bubbles in the aqueous suspension of dinoflagellates.

5. The system of claim 4, further comprising a transparent sample container configured to contain the aqueous solution and the test sample inside the test chamber.

6. The system of claim 5, wherein the sample container has a lower end and the gas is introduced into the aqueous suspension in the sample container in the lower end.

7. The system of claim 4, further comprising a cartridge configured to be supported inside the test chamber, the cartridge comprising an array of transparent sample containers, each transparent sample container containing a generally equal amount of the aqueous suspension of dinoflagellates.

8. The system of claim 7, wherein the cartridge further comprises an array of optical isolation silos configured to optically isolate the transparent sample containers from each other, and wherein each optical isolation silo comprises an optical window through which the excitation signal, the fluorescence signal and the bioluminescence signal may pass.

9. The system of claim 8, wherein only one optical window is optically aligned with the first and second optical transducers such that generally only the fluorescence and bioluminescence signals emanating from one sample container may be detected by the first and second optical transducers respectively.

10. The system of claim 9, further comprising an actuator configured to reposition the cartridge such that each of the optical windows in turn may be optically aligned with the first and second optical transducers.

11. The system of claim 10, further comprising a test sample distributor configured to distribute an amount of the test sample into each of the sample containers.

12. The system of claim 11, wherein the cartridge further comprises a cartridge cover configured to cover each of the transparent sample containers, the cartridge cover comprising a vent and a gas tube for each of the transparent sample containers.

13. The system of claim 12, wherein each of the transparent sample containers has a lower end and each gas tube from the cartridge cover extends into the lower end of the corresponding transparent sample container.

14. The system of claim 13, wherein the cartridge cover further comprises a bar code mounted on an outer surface of the cartridge cover, wherein the bar code contains cartridge identification information.

15. The system of claim 14, further comprising a bar code scanner configured to scan the bar code and to convey cartridge identification information to the processor.

16. The system of claim 14, wherein the cartridge is designed to be disposable after a single use.

17. The system of claim 12, wherein the test sample distributor is disposed to distribute an amount of the test sample into each of the sample containers through each test sample container's corresponding vent.

* * * * *